United States Patent [19]
Ohmori et al.

[11] Patent Number: 5,590,661
[45] Date of Patent: Jan. 7, 1997

[54] BLOOD PRESSURE MEASURING APPARATUS

[75] Inventors: Kenji Ohmori, Yokohama; Kiyoyuki Narimatsu, Kasugai, both of Japan; Ikuo Kobayashi, Vanimo, Papua New Guinea

[73] Assignee: Colin Corporation, Komaki, Japan

[21] Appl. No.: 282,230

[22] Filed: Jul. 29, 1994

[51] Int. Cl.$^6$ .................................................. A61B 5/02
[52] U.S. Cl. ......................................... 128/672; 128/687
[58] Field of Search ................................... 128/672, 677, 128/680, 681, 682, 683, 687, 688, 690

[56] References Cited

U.S. PATENT DOCUMENTS

| | | | |
|---|---|---|---|
| 4,271,843 | 6/1981 | Flynn | 128/681 |
| 4,427,013 | 1/1984 | Nunn et al. | 128/681 |
| 4,799,491 | 1/1989 | Eckerle | 128/672 |
| 4,836,213 | 6/1989 | Wenzel et al. | 128/672 |
| 4,928,700 | 5/1990 | Harada | 128/672 |
| 5,119,822 | 6/1992 | Niwa | 128/672 |
| 5,183,050 | 2/1993 | Kawamura | 128/672 |

FOREIGN PATENT DOCUMENTS

1-161707  11/1989  Japan .

*Primary Examiner*—Angela D. Sykes
*Assistant Examiner*—Eric F. Winakur
*Attorney, Agent, or Firm*—Oliff & Berridge

[57] ABSTRACT

A blood pressure measuring apparatus including a surface-pressure sensor having a pressure sensing element in a press surface thereof to detect a pressure at the press surface pressed on subject's body surface and generate a pressure signal representing the detected surface pressure, the pressure signal containing successive pulses representing a pressure pulse wave produced from subject's artery, a pressing device which presses the sensor against the artery via the body surface, a control device which changes the pressing force of the pressing device applied to the sensor, to partially flatten the artery, and obtains the successive pulses of the pressure signal during the changing of the pressing force, a first determining device for determining, in a two-dimensional orthogonal coordinate system, a first straight line approximating a level portion of (a) an upper-peak curve connecting respective upper-peak magnitudes of the successive pulses of the pressure signal and/or (b) a lower-peak curve connecting respective lower-peak magnitudes of the successive pulses, a second determining device for determining a second straight line approximating an increasing portion of (a) the upper-peak curve and/or (b) the lower-peak curve, and a blood pressure determining device for determining a systolic and/or a diastolic blood pressure of the subject based on an intersecting point of the first and second straight lines.

20 Claims, 3 Drawing Sheets

BLOOD PRESSURE MEASURING APPARATUS

BACKGROUND OF THE INVENTION

1. Field of the Invention

The present invention relates to a blood pressure measuring apparatus including a surface-pressure sensor adapted to be pressed against an artery of a living body or subject via a body surface of the subject.

2. Related Art Statement

There is known a blood pressure (BP) measuring device which non-invasively measures a BP value of a living subject based on a pulse-sound signal or a pulse-wave signal which is continuously obtained while an inflatable cuff wound around subject's body portion such as an upper arm is inflated, or is deflated after being inflated, to press the body portion. The non-invasively measured BP value is an approximation of an intra-arterial BP value directly or invasively measured from inside an artery of the subject.

In the conventional BP measuring device, however, the cuff presses the subject's body portion all around with a considerably great force, so that the subject may suffer the discomfort due to the use of the cuff.

Meanwhile, Unexamined Japanese Utility Model Application laid open under Publication No. 1(1989)-161707 discloses a blood pressure (BP) monitor including (a) an inflatable cuff, (b) a fluid supply which supplies a pressurized fluid to the cuff, (c) a control device which changes the fluid pressure in the cuff, (d) a surface-pressure sensor adapted to be pressed on subject's body surface to detect a pressure pulse wave produced from subject's artery and generate a pressure signal representing the detected pulse wave, and (e) BP determining means for determining a BP value of the subject, based on each of successive pulses contained in the pressure signal, according to a relationship between blood pressure (BP) and pressure signal (PS). In the BP monitor, the BP-PS relationship is determined, and updated, based on the standard BP values periodically measured using the cuff. The cuff is necessary to measure the standard BP values used for calibrating the pressure signal of the surface-pressure sensor, because the accuracy of the BP measurement using the surface-pressure sensor is not satisfactorily high.

SUMMARY OF THE INVENTION

It is therefore an object of the present invention to provide a blood pressure measuring apparatus which provides a good approximation of an intra-arterial blood pressure of a living subject, by using a surface-pressure sensor adapted to be pressed against subject's artery via subject's body surface.

The above object has been achieved by the present invention, which provides a blood pressure measuring apparatus, comprising: (A) a surface-pressure sensor having a press surface adapted to be pressed on a body surface of a living subject, and including at least one pressure sensing element provided in the press surface to detect a pressure at the press surface pressed on the body surface and generate a pressure signal representing the detected pressure, the pressure signal containing a plurality of successive pulses representing a pressure pulse wave which is produced from an artery of the subject under the body surface in synchronism with heartbeat of the subject and is propagated to the press surface of the sensor via the body surface; (B) a pressing device which presses the surface-pressure sensor against the artery via the body surface; (C) a control device which changes a pressing force of the pressing device applied to the surface-pressure sensor, to partially flatten the artery under the sensor, and obtains the successive pulses of the pressure signal from the sensor while the pressing force of the pressing device is changed; (D) first straight line determining means for determining, in a two-dimensional orthogonal coordinate system defined by a first axis indicative of pressing forces of the pressing device and a second axis indicative of magnitudes of the pressure signal, a first straight line approximating a level portion of at least one of (a) an upper-peak curve which connects respective upper-peak magnitudes of the successive pulses of the pressure signal obtained by the control device, and (b) a lower-peak curve which connects respective lower-peak magnitudes of the successive pulses, the level portion corresponding to a first range of pressing forces of the pressing device; (E) second straight line determining means for determining, in the two-dimensional orthogonal coordinate system, a second straight line approximating an increasing portion of the at least one of (a) the upper-peak curve and (b) the lower-peak curve, the increasing portion corresponding to a second range of pressing forces of the pressing device which are greater than the first range of pressing forces; and (F) blood pressure determining means for determining at least one of a systolic and a diastolic blood pressure of the subject based on an intersecting point of the first and second straight lines determined by the first and second straight line determining means.

In the blood pressure (BP) measuring apparatus constructed as described above, the blood pressure (BP) determining means determines a systolic and/or a diastolic BP value of a subject based on an intersecting point of the first and second straight lines determined by the first and second straight line determining means. The thus determined BP values accurately correspond to the intra-arterial BP values invasively measured in an artery of the subject. Since the present apparatus uses no inflatable cuff, the subject is free from the discomfort due to the use of the cuff. The surface-pressure sensor is employed in place of the cuff. The sensor is adapted to be pressed locally on the body surface directly above the artery, unlike the cuff that is wound around subject's body portion such as an upper arm to press the body portion all around with a considerably great force. Thus, the use of surface-pressure sensor does not result in causing the subject to feel any discomfort.

According to a preferred feature of the present invention, the control device comprises reference pressing force determining means for determining a reference pressing force of the pressing device based on respective amplitudes of the successive pulses of the pressure signal obtained while the pressing force of the pressing device is changed; and pressing force holding means for holding the pressing force of the pressing device at the reference pressing force at which the pressure sensing element of the surface-pressure sensor detects the pressure pulse wave produced from the artery of the subject and generates the pressure signal representing the detected pressure pulse wave.

According to another feature of the present invention, the blood pressure determining means further comprises relationship determining means for determining a relationship between blood pressure values and magnitudes of the pressure signal, based on the at least one of the systolic and diastolic blood pressure values of the subject and at least one of an upper-peak and a lower-peak magnitude of a pulse of the pressure signal generated by the surface-pressure sensor when the pressing force of the pressing device is held at the reference pressing force. This apparatus functions as a non-invasive continuous BP monitor. Since the systolic and/or diastolic BP values determined by the present BP monitor are a good approximation of intra-arterial systolic and diastolic blood pressure values, no cuff is necessary to measure the standard BP values based on which a relationship between blood pressure and pressure signal is determined as taught by the previously-identified Japanese Utility Model Application. Additionally, the present BP monitor does not need a control device for changing the cuff pressure to measure the standard BP values. Therefore, the non-invasive BP monitor may be constructed in a small size and produced at a low cost.

BRIEF DESCRIPTION OF THE DRAWINGS

The above and optional objects, features, and advantages of the present invention will be better understood by reading the following detailed description of the preferred embodiments of the invention when considered in conjunction with the accompanying drawings, in which.

DETAILED DESCRIPTION OF THE PREFERRED EMBODIMENTS

Figure 1:
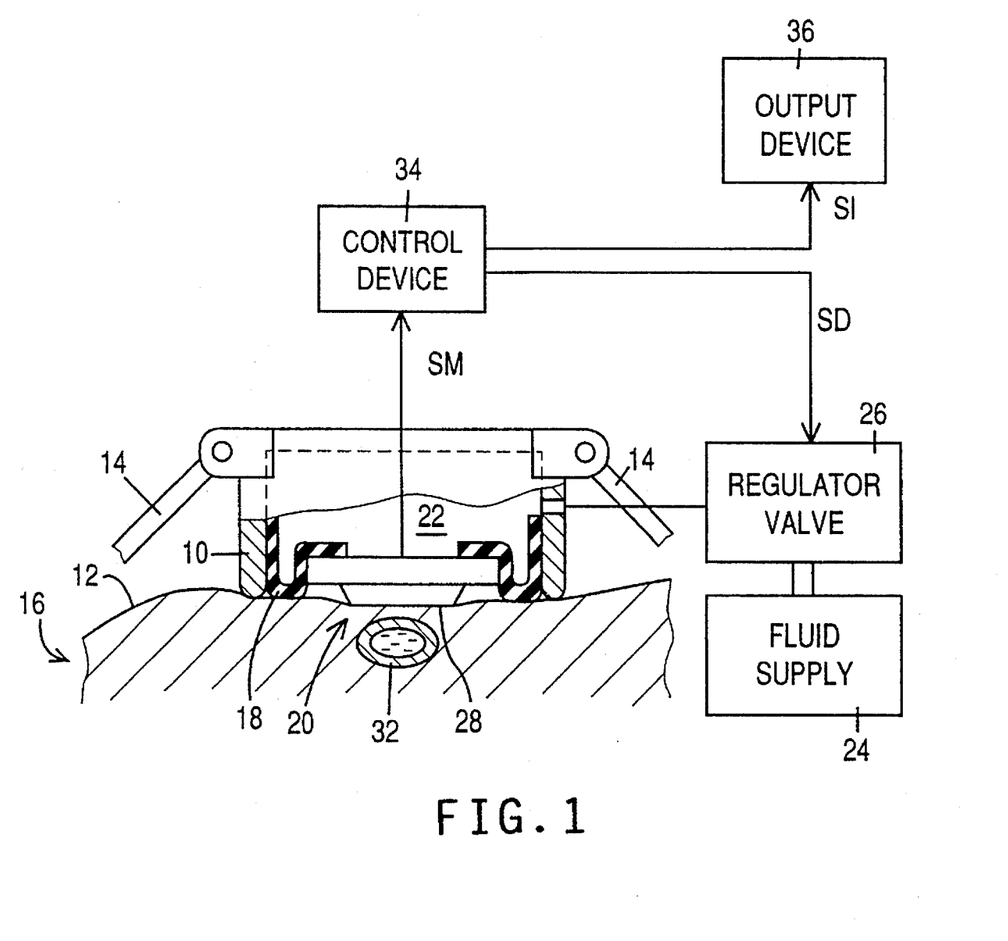
FIG. 1 is a diagrammatic view of the basic construction of a blood pressure measuring apparatus embodying the present invention.

Referring to FIG. 1, there is shown a blood pressure (BP) measuring apparatus embodying the present invention. The present apparatus provides a non-invasive continuous BP monitor which non-invasively and continuously measures the BP values of a human being or living subject based on each of successive pulses of a pressure pulse wave produced from an artery of the subject.

In FIG. 1, reference numeral 10 designates a cylindrical housing which has a bottom wall at one end and is open at the other end. The housing 10 is detachably set on a body surface 12 of a wrist 16 of the subject, with a pair of setting bands 14, 14, such that the open end of the housing 10 is held in pressed contact with the body surface 12. A surface-pressure sensor 20 is secured via an elastic diaphragm 18 to inner surfaces of the housing 10, such that the sensor 20 is displaceable relative to the housing 10 and is advanceable out of the open end of the same 10. The housing 10, diaphragm 18, and sensor 20 cooperate with each other to define a pressure chamber 22. The pressure chamber 22 is supplied with a pressurized fluid such as a pressurized air from a fluid supply 24 via a pressure regulator valve 26. Thus, the surface-pressure sensor 20 is pressed on the body surface 12, with a pressing force corresponding to a fluid pressure in the pressure chamber 22 (hereinafter, referred to as the "chamber pressure P").

The surface-pressure sensor 20 includes a semiconductor chip formed of monocrystalline silicon, for example. The semiconductor chip has a press surface 28 in which a plurality of pressure sensing elements (e.g., pressure sensing diodes, not shown) are provided in an array. When the sensor 20 is set on the wrist 16 with the bands 14, 14, the array of pressure sensing elements almost orthogonally intersects a radial artery 32 running under the body surface 12. When the sensor 20 is pressed against the radial artery 32 via the body surface 12 by the diaphragm 18 being inflated, each of the pressure sensing elements of the sensor 20 detects a pressure at the press surface 28 and generates a pressure signal, SM, to a control device 34 via an analog to digital converter (not shown).

The pressure signal SM contains a plurality of successive pulses representing a pressure pulse wave which is produced from the radial artery 32 in synchronism with heartbeat of the subject and is propagated to the press surface 28 via the body surface 12. The pressure sensing elements of the sensor 20 have a size and a pitch (i.e., distance between each pair of adjacent elements) which assure that a plurality of pressure sensing elements can be located on a local portion of the body surface 12 directly above the radial artery 32.

The control device 34 is essentially constituted by a microcomputer including a central processing unit (CPU), a read only memory (ROM), a random access memory (RAM), and an input and output (I/O) port. The CPU processes the respective pressure signals SM from the pressure sensing elements of the surface-pressure sensor 20, by utilizing the temporary-storage function of the RAM, according to the control program pre-stored in the ROM. The CPU generates, via the I/O port, a drive signal, SD, to the pressure regulator valve 26 so as to regulate the fluid pressure in the pressure chamber 22, i.e., chamber pressure P. While the CPU operates the regulator valve 26 for increasing the chamber pressure P, the CPU collects the respective pressure signals SM from the pressure sensing elements of the surface-pressure sensor 20. Based on the collected pressure signals SM, the CPU selects a reference pressure sensing element from the pressure sensing elements of the sensor 20.

The CPU determines a systolic, SYS, and a diastolic, DIA, blood pressure (BP) value of the subject, based on (a) an upper-peak curve connecting the respective upper-peak magnitudes of the successive pulses of the pressure signal SM obtained from the reference pressure sensing element while the chamber pressure P is increased and (b) a lower-peak curve connecting the respective lower-peak magnitudes of the same successive pulses of the pressure signal SM. Additionally, the CPU determines a reference pressure value Pref of the chamber pressure P, as a reference pressing force applied to the surface-pressure sensor 20, according to the control program pre-stored in the ROM, and holds the pressure chamber 22 at the thus determined reference pressure value Pref.

Furthermore, the CPU determines a relationship between blood pressure values and magnitudes of pressure signal SM, based on the BP values SYS, DIA determined based on the upper-peak and lower-peak curves, and based on an upper-peak and a lower-peak magnitude of a pulse of the pressure signal SM supplied from the reference pressure sensing element when the pressure chamber 22 is held at the reference pressure value. The CPU determines a systolic and a diastolic BP value of the subject according the thus determined relationship based on each of the successive pulses of the pressure signal SM from the reference pressure sensing element while the pressure chamber 22 is held at the reference pressure value Pref.

The CPU generates, via the I/O port, an output signal, SI, to an output device 36 so that the output device 36 successively displays the thus determined BP values and records the same on a recording medium (e.g., record sheet). The output device 36 includes an image display (e.g., cathode ray tube) for displaying the BP values, and a printer for recording the same on a record sheet. In the present invention, the housing 10, diaphragm 18, fluid supply 24, and regulator valve 26 cooperate with each other to provide a pressing device which presses the surface-pressure sensor 20 against the radial artery 32 via the body surface 12.

There will be described the operation of the BP measuring apparatus constructed as described above, by reference to the flow chart of FIG. 2.

Figure 2:
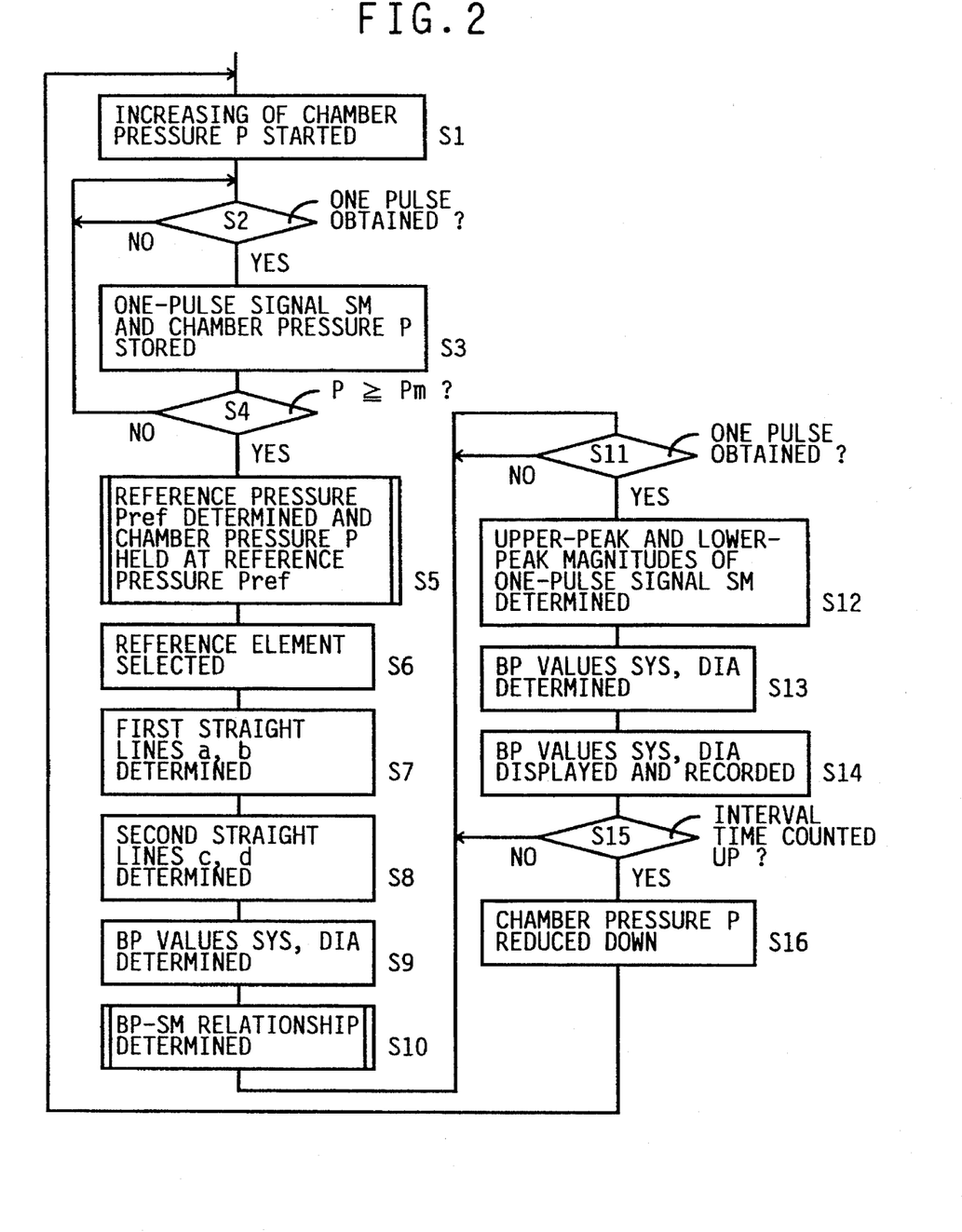
FIG. 2 is a flow chart representing a control program according to which the apparatus of FIG. 1 operates for measuring a bloodpressure of a living subject.

First, at Step S1, the CPU of the control device 34 controls the pressure regulator valve 26 for increasing the fluid pressure in the pressure chamber 22, i.e., chamber pressure P at a predetermined low rate. Step S1 is followed by Step S2 to judge whether the CPU has read in a span of pressure signal SM corresponding to one pulse, i.e., one heartbeat of the subject, from each of the pressure sensing elements of the surface-pressure sensor 20. If a negative judgment is made at Step S2, the CPU repeats this step. Meanwhile, if a positive judgment is made at Step S2, the control of the CPU proceeds with Step S3 to store, in the RAM, the one-pulse signals SM and a chamber pressure P at the time of detection of the one-pulse signals SM.

Step S3 is followed by Step S4 to judge whether the chamber pressure P has reached a predetermined target pressure, Pm (e.g., 200 mmHg). If a negative judgment is made at Step S4, the control of the CPU goes back to Step S2 and the following steps. If a positive judgement is made at Step S4 while the CPU repeats Steps S2 through S4, the control of the CPU goes to Step S5.

At Step S5, the CPU stops increasing the chamber pressure P and determines, as a reference chamber pressure Pref, a chamber pressure P at the time of detection of a pulse having the greatest amplitude of all the amplitudes of the respective pulses of the pressure signals SM from the pressure sensing elements of the surface-pressure sensor 20. The reference chamber pressure Pref corresponds to a reference pressing force applied to the sensor 20 to partially flatten the radial artery 32. The CPU holds the pressure chamber 22 at the thus determined reference pressure value Pref. Step S5 is followed by Step S6 to select, from the plurality of pressure sensing elements of the sensor 20, a reference pressure sensing element which has generated the above-described pulse having the greatest amplitude.

Figure 3:
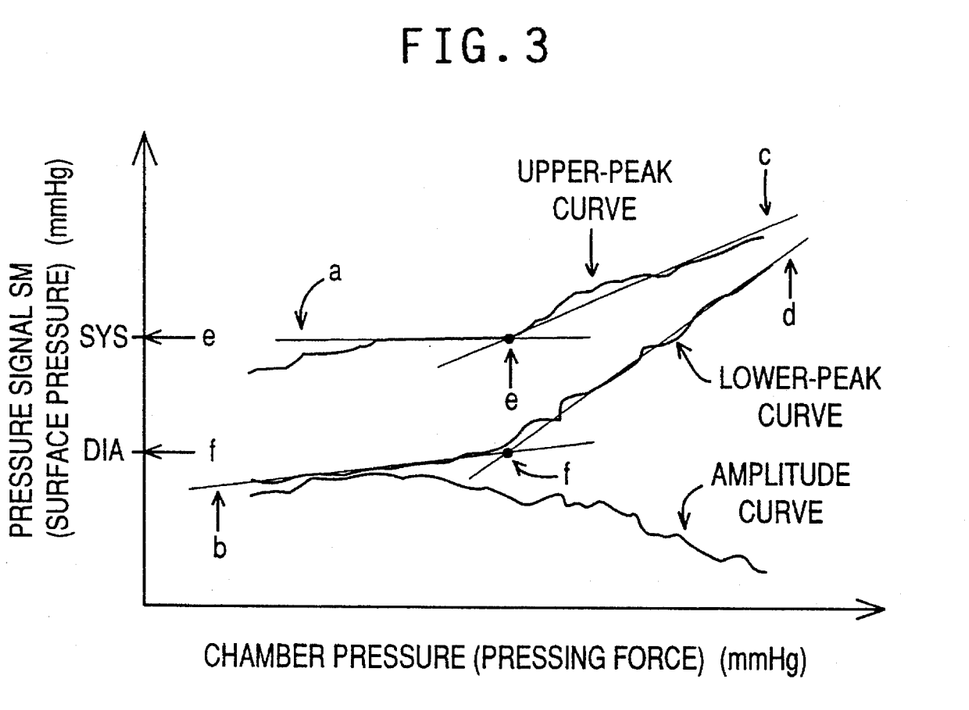
FIG. 3 is a graph representing a two-dimensional orthogonal coordinate system in which are plotted an upper-peak curve and a lower-peak curve each obtained from the successive pulses of a pressure signal SM which is continuously supplied from a reference pressure sensing element while a pressing force P applied to a surface-pressure sensor of the apparatus of FIG. 1 is increased according to the flow chart of FIG. 2.

FIG. 3 shows a two-dimensional orthogonal coordinate system defined by a first axis indicative of chamber pressure P (mmHg) and a second axis indicative of pressure signal SM (mmHg). The chamber pressure P (mmHg) represents the pressing force applied to the surface-pressure sensor 20, and the pressure signal SM represents the pressure (mmHg) at the press surface 28 detected by the sensor 20 (or reference pressure sensing element). In the coordinate system, are plotted (a) an upper-peak curve which connects the respective upper-peak magnitudes of the successive pulses of the pressure signal SM supplied from the reference pressure sensing element while the chamber pressure P is increased at the low rate at Steps 1 through S4; (b) a lower-peak curve which connects the respective lower-peak magnitudes of the same successive pulses; and (c) an amplitude curve which connects the respective amplitudes of the same successive pulses. The amplitude of each pulse is obtained by subtracting the lower-peak magnitude of the pulse from the upper-peak magnitude of the same.

Step S6 is followed by Step S7 to determine a first straight line, a (FIG. 3), approximating a level 10 portion of (a) the upper-peak curve, and determine a first straight line, b, approximating a level portion of (b) the lower-peak curve. More specifically, the CPU determines, for the level portion of (a) the upper-peak curve, a first pressure range which has an upper limit greater by a first predetermined amount (e.g., 1 to 3 mmHg) than a reference pressure represented by a magnitude of the upper-peak curve corresponding to the reference chamber pressure Pref, and has a lower limit smaller by a second predetermined amount (e.g., 1 to 3 mmHg) than the reference pressure, and determines, as the level portion of (a) the upper-peak curve, a portion of (a) the upper-peak curve which corresponds to the first pressure range. The CPU determines, as the first straight line a, a regression line of the level portion of (a) the upper-peak curve, according to the known mathematical or statistical technique. Similarly, the CPU determines, for the level portion of (b) the lower-peak curve, a second pressure range which has an upper limit greater by a third predetermined amount (e.g., 1 to 3 mmHg) than a reference pressure represented by a magnitude of the lower-peak curve corresponding to the reference chamber pressure Pref, and has a lower limit smaller by a fourth predetermined amount (e.g., 1 to 3 mmHg) than the reference pressure, and determines, as the level portion of (b) the lower-peak curve, a portion of (b) the lower peak curve which corresponds to the second pressure range. The CPU determines, as the first straight line b, a regression line of the level portion of (b) the lower-peak curve according to the same statistical technique.

At the following Step S8, the CPU determines, in the two-dimensional orthogonal coordinate system of FIG. 3, a second straight line, c, approximating an increasing portion of (a) the upper-peak curve and determines a second straight line, d, approximating an increasing portion of (b) the lower-peak curve. More specifically, the CPU determines, for the increasing portion of (a) the upper-peak curve, a third pressure range which has a lower limit greater by a fifth predetermined amount (e.g., 3 mmHg) than the upper limit of the first pressure range for the level portion of (a) the upper-peak curve, and has an upper limit represented by a magnitude of (a) the upper-peak curve corresponding to the predetermined target pressure Pm used at Step S4, and determines, as the increasing portion of (a) the upper-peak curve, a portion of (a) the upper-peak curve which to the same statistical technique.

At the following Step S8, the CPU determines, in the two-dimensional orthogonal coordinate system of FIG. 3, a second straight line, c, approximating an increasing portion of (a) the upper-peak curve and determines a second straight line, d, approximating an increasing portion of (b) the lower-peak curve. More specifically, the CPU determines, for the increasing portion of (a) the upper-peak curve, a third pressure range which has a lower limit greater by a fifth predetermined amount (e.g., 3 mmHg) than the upper limit of the first pressure range for the level portion of (a) the upper-peak curve, and has an upper limit represented by a magnitude of (a) the upper-peak curve corresponding to the predetermined target pressure Pm used at Step S4, and determines, as the increasing portion of (a) the upper-peak curve, a portion of (a) the upper-peak curve which corresponds to the third pressure range. Similarly, the CPU determines, for the increasing portion of (b) the lower-peak curve, a fourth pressure range which has a lower limit greater by a sixth predetermined amount (e.g., 3 mmHg) than the upper limit of the second pressure range for the level portion of (b) the lower-peak curve, and has an upper limit represented by a magnitude of (b) the lower-peak curve corresponding to the predetermined target pressure Pm, and determines, as the increasing portion of (b) the lower-peak curve, a portion of (b) the lower-peak curve which corresponds to the fourth pressure range. The CPU determines, as the second straight line c, a regression line of the increasing portion of (a) the upper-peak curve and determines, as the second straight line d, a regression line of the increasing portion of (b) the lower-peak curve, each according to the known statistical technique.

In the graph of FIG. 3, as the chamber pressure P increases, the two increasing portions of (a) the upper-peak curve and (b) the lower-peak curve converge toward each other. This convergence indicates that the radial artery 32 is partially flattened under the surface-pressure sensor 20 being pressed with the chamber pressure P.

At the following Step S9, the CPU determines, as a systolic blood pressure SYS of the subject, a pressure corresponding to an intersecting point, e (FIG. 3), of the first and second straight lines a and c determined on (a) the upper-peak curve and determines, as a diastolic blood pressure DIA of the subject, a pressure corresponding to an intersecting point, f, of the first and second straight lines b and d determined on (b) the lower-peak curve.

Step S9 is followed by Step S10 to read in a span of pressure signal SM corresponding to one pulse or one heartbeat of the subject, from the reference pressure sensing element pressed at the reference chamber pressure Pref, and determine an upper-peak and a lower-peak magnitude of the one-pulse signal SM. The CPU determines, as a relationship between blood pressure (BP) and pressure signal magnitude (SM), a linear function: $BP = \alpha \cdot SM + \beta$, by (a) replacing the two variables BP, SM by the value SYS and the upper-peak magnitude, respectively, (b) replacing the two variables BP, SM by the value DIA and the lower-peak magnitude, respectively, and (c) solving the thus obtained simultaneous equations including the two unknowns $\alpha$, $\beta$.

Once the BP-SM relationship between blood pressure and pressure signal magnitude is obtained, the CPU starts a continuous BP monitoring based on each of successive pulses of the pressure signal SM supplied from the surface-pressure sensor 20. At the following Step S11, the CPU judges whether the CPU has read in a span of pressure signal SM corresponding to one pulse of the pressure pulse wave of the subject. If a positive judgment is made at Step S11, the control of the CPU goes to Step S12 to determine the upper-peak and lower-peak magnitudes of the one-pulse signal SM. Step S12 is followed by Step S13 to determine a systolic and a diastolic BP value of the subject based on the upper-peak and lower-peak magnitudes determined at Step S12 according to the linear function determined at Step S10. At the following Step S14, the CPU operates the output device 36 to display and record the determined BP values. Step S14 is followed by Step S15 to judge whether a timer has counted up a predetermined interval time (e.g., 15 minutes). So long as a negative judgment continues at Step S15, the CPU repeats Steps S11 through S15 so as to determine a systolic and a diastolic BP value of the subject based on each of 10 successive pulses of the pressure signal SM supplied from the reference pressure sensing element, according to the linear function determined at Step S10. Meanwhile, if a positive judgment is made at Step S15, the control of the CPU goes to Step S16 to reset the contents of the timer to zero, and deflate the pressure chamber 22, thereby reducing down the chamber pressure P. Following Step S16, the control of the CPU returns to Step S1. In the following control cycle, the CPU re-determines the BP values SYS, DIA of the subject based on the upper-peak and lower-peak curves newly obtained during the process of increasing the chamber pressure P, updates the BP-SM relationship (i.e., linear function), and determines the systolic and diastolic BP values of the subject based on each of successive pulses of the pressure signal SM.

As is apparent from the foregoing description, in the present embodiment, the control device (or the CPU thereof) reads in the pressure signal SM which is continuously supplied from the surface-pressure sensor 20 (or the reference pressure sensing element) in the process of increasing the pressing force (i.e., chamber pressure P) applied to the sensor 20 and partially flattening the wall of radial artery 32 (as shown in FIG. 1). The CPU determines the systolic BP value SYS of the subject based on the intersecting point e of the first and second straight lines a, c determined on the upper-peak curve obtained by connecting the respective upper-peak magnitudes of the successive pulses contained in the read-in pressure signal SM, and also determines the diastolic BP value DIA of the subject based on the intersecting point f of the first and second straight lines b, d determined on the lower-peak curve obtained by connecting the respective lower-peak magnitudes of the successive pulses of the read-in pressure signal SM. The intersecting points e, f determined with respect to the upper-peak and lower-peak curves correspond to the pressing force (i.e., chamber pressure P) at which the wall of radial artery 32 is partially flattened. The two pressure values represented by the respective signal magnitudes of the two intersecting points e, f accurately correspond to the actual systolic and diastolic BP values inside the radial artery 32, i.e., intra-arterial systolic and diastolic BP values, respectively. Since in the present embodiment no inflatable cuff is employed, the subject is free from the discomfort due to the use of a cuff. In the present embodiment, the surface-pressure sensor 20 is employed in place of a cuff. The sensor 20 is adapted to be pressed locally on the body surface 12 directly above the radial artery 32, unlike a cuff that is adapted to be wound fully around a body portion such as an upper arm so as to completely stop the blood flow through the brachial artery of a subject. In contrast, according to the principle of the present invention, the wall of an artery (e.g., radial artery 32) is not completely flattened to stop the blood flow therethrough. Thus, the use of the surface-pressure sensor 20 does not cause the subject to feel so serious discomfort.

Additionally, in the present embodiment, the BP-SM relationship is obtained based on the accurate BP values SYS, DIA determined based on the upper-peak and lower-peak curves, and the BP-SM relationship is used for determining the systolic and diastolic BP values of the subject based on each of successive pulses of the pressure signal SM, i.e., pressure pulse wave of the subject. Unlike the conventional device disclosed by Japanese Utility Model Application laid open under Publication No. 1-161707, the present apparatus does not need an inflatable cuff for measuring standard BP values used for determining or updating a BP-SM relationship. Therefore, the present apparatus does not need a supply device for supplying a pressure to the cuff, or a control device for regulating the pressure in the cuff. Thus, the present non-invasive continuous BP monitor may be produced at reduced size and cost.

While the present invention has been described in its preferred embodiment, the present invention may otherwise be embodied.

In the illustrated embodiment, the BP values SYS, DIA of the subject are determined based on the intersecting point e of the first and second straight lines a, c of the upper-peak curve, and the intersecting point f of the first and second straight lines b, d of the lower peak curve, both of which curves are obtained from the pressure signal SM 10 supplied from the reference pressure sensing element, and the BP-SM relationship is determined based on the thus determined BP values SYS, DIA. However, other methods may be employed. For example, it is possible to additionally determine, in the same way, BP values SYS, DIA by using the pressure signal SM supplied from each of the two pressure sensing elements adjacent to, and on both sides of, the reference element, and calculate respective averages of the three values SYS and the three values DIA. In the latter case, the BP-SM relationship is determined based on the average systolic and diastolic BP values SYS, DIA.

In the illustrated embodiment, the BP-SM relationship is determined based on both of the two BP values SYS, DIA obtained from the upper-peak and lower-peak curves and both of the upper-peak and lower-peak magnitudes of one pulse of the pressure signal SM obtained at the reference chamber pressure Pref. However, it is possible to determine only one of the BP values SYS, DIA and additionally determine a mean BP value, MEAN, of the subject by utilizing the gravity center of the area enveloped by (a) the one-pulse signal SM obtained at the reference chamber pressure Pref and (a) the base line of the one-pulse signal SM. In the latter case, the BP-SM relationship is determined based on the determined one of the BP values SYS, DIA and the determined BP value MEAN.

In the flow chart of FIG. 2, it is possible to omit Steps S10 to S15. In this case, Step S9 is modified such that the CPU operates the output device 36 to display and record the determined BP values SYS, DIA. Furthermore, in this case, one of Steps S7 and S8 may be omitted. In the last case, Step S9 is modified such that the CPU determines one of the BP values SYS, DIA, and the output device 36 outputs the determined one BP value.

In the flow chart of FIG. 2, it is also possible to add, between Steps S6 and S7, a step where the CPU judges whether the upper-peak and lower-peak curves converges toward each other, based on change of the difference of the two curves. If a negative judgment is made at the additional step, the control of the CPU does not go to Steps S6 through S9. In the event that the radial artery 32 is moved deeply in the wrist 16 when the surface-pressure sensor 20 is pressed and therefore the same 32 is not flattened, a negative judgment is made, and an alarm sound is issued to inform the operator of this situation. Thus, an inaccurate blood pressure measurement is avoided.

In the illustrated embodiment, one of the pressure sensing elements which one element has supplied a pulse having the greatest amplitude, is selected as the reference pressure sensing element. Alternatively, the reference pressure sensing element may be selected as one of the pressure sensing elements which has supplied a pressure signal SM showing the smallest difference between a base line thereof at the start of increasing of the chamber pressure P and a base line thereof at a predetermined, increased level of the chamber pressure P.

Although in the illustrated embodiment a plurality of pressure sensing elements are provided in the press surface 28 of the surface-pressure sensor 20, a single pressure sensing element may be provided in the press surface 28. In the latter case, too, the present apparatus enjoys substantially the same advantages as described above.

While in the illustrated embodiment the BP values SYS, DIA are determined based on the pressure signal SM obtained while the chamber pressure P is increased, it is possible to utilize, for the same purpose, the pressure signal SM obtained while the chamber pressure P is decreased.

Although in the illustrated embodiment the surface-pressure sensor 20 is adapted to be pressed against the radial artery 32, the sensor 20 may be modified to be pressed against a different artery such as a pedal dorsal artery.

It is to be understood that the present invention may be embodied with other changes, improvements, and modifications that may occur to those skilled in the art without departing from the spirit and scope of the invention defined in the appended claims.

What is claimed is:

1. A blood pressure measuring apparatus, comprising:

a surface-pressure sensor having a press surface adapted to be pressed on a body surface of a living subject, and including at least one pressure sensing element provided in said press surface to detect a pressure at said press surface pressed on the body surface and generate a pressure signal representing the detected pressure, said pressure signal containing a plurality of successive pulses representing a pressure pulse wave which is produced from an artery of the subject under the body surface in synchronism with heartbeat of the subject and is propagated to said press surface of said sensor via the body surface;

a pressing device which generates a pressing force to press said surface-pressure sensor against the artery via the body surface;

a control device which changes the pressing force of said pressing device applied to said surface-pressure sensor, to partially flatten the artery under said sensor, and obtains the successive pulses of said pressure signal from said sensor while said pressing force of said pressing device is changed;

first straight line determining means for determining, in a two-dimensional orthogonal coordinate system defined by a first axis indicative of pressing forces of said pressing device and a second axis indicative of magnitudes of said pressure signal, a first straight line approximating a level portion of at least one of (a) an upper-peak curve which connects respective upper-peak magnitudes of said successive pulses of said pressure signal obtained by said control device, and (b) a lower-peak curve which connects respective lower-peak magnitudes of said successive pulses, said level portion corresponding to a first range of pressing forces of said pressing device;

second straight line determining means for determining, in said two-dimensional orthogonal coordinate system, a second straight line approximating an increasing portion of said at least one of (a) said upper-peak curve and (b) said lower-peak curve, said increasing portion corresponding to a second range of pressing forces of said pressing device which are greater than said first range of pressing forces; and blood pressure determining means for determining at least one of a systolic and a diastolic blood pressure of the subject based on an intersecting point of said first and second straight lines determined by said first and second straight line determining means.

2. An apparatus according to claim 1, wherein said blood pressure determining means comprises means for determining, as said systolic blood pressure of the subject, a pressure corresponding to said intersecting point of said first straight line approximating said level portion of (a) said upper-peak curve and said second straight line approximating said increasing portion of (a) the upper-peak curve.

3. An apparatus according to claim 1, wherein said blood pressure determining means comprises means for determining, as said diastolic blood pressure of the subject, a pressure corresponding to said intersecting point of said first straight line approximating said level portion of (b) said lower-peak curve and said second straight line approximating said increasing portion of (b) the lower-peak curve.

4. An apparatus according to claim 1, wherein said control device comprises:
reference pressing force determining means for determining a reference pressing force of said pressing device based on respective amplitudes of said successive pulses of said pressure signal obtained while said pressing force of said pressing device is changed; and
pressing force holding means for holding said pressing force of said pressing device at said reference pressing force at which said pressure sensing element of said surface-pressure sensor detects said pressure pulse wave produced from the artery of the subject and generates said pressure signal representing the detected pressure pulse wave.

5. An apparatus according to claim 4, wherein said reference pressing force determining means comprises means for determining, as said reference pressing force of said pressing device, a pressing force of said pressing device at a time when a greatest one of said respective amplitudes of said successive pulses of said pressure signal is obtained while said pressing force of said pressing device is changed.

6. An apparatus according to claim 4, wherein said blood pressure determining means further comprises relationship determining means for determining a relationship between blood pressure values and magnitudes of said pressure signal, based on said at least one of said systolic and said diastolic blood pressure of the subject and at least one of an upper-peak and a lower-peak magnitude of a pulse of said pressure signal generated by said surface-pressure sensor when said pressing force of said pressing device is held at said reference pressing force.

7. An apparatus according to claim 6, wherein said relationship determining means comprises function determining means for determining a linear function as said relationship between blood pressure values and magnitudes of said pressure signal.

8. An apparatus according to claim 4, wherein said control device further comprises means for selecting, as a reference pressure sensing element, one of a plurality of pressure sensing elements as said at least one pressure sensing element of said surface-pressure sensor, such that said one pressure sensing element generates a pressure signal containing a pulse having a greatest amplitude, out of said plurality of pressure sensing elements, when said pressing force of said pressing device is held at said reference pressing force.

9. An apparatus according to claim 1, wherein said first straight line determining means comprises:
first pressure range determining means for determining a first pressure range based on said successive pulses of said pressure signal obtained by said control device while said pressing force of said pressing device is changed; and
level portion determining means for determining, as said level portion of said at least one of (a) said upper-peak curve and (b) said lower-peak curve, a portion of said at least one of (a) said upper-peak curve and (b) said lower-peak curve which portion corresponds to said first pressure range.

10. An apparatus according to claim 9, wherein said control device comprises reference pressing force determining means for determining a reference pressing force of said pressing device based on respective amplitudes of said successive pulses of said pressure signal obtained while said pressing force of said pressing device is changed; and
said first pressure range determining means determining said first pressure range which contains a reference pressure represented by a magnitude of said level portion corresponding to said reference pressing force determined by said reference pressing force determining means.

11. An apparatus according to claim 10, wherein said first pressure range determining means comprises means for determining said first pressure range which has an upper limit greater by a first predetermined amount than said reference pressure, and a lower limit smaller by a second predetermined amount than said reference pressure.

12. An apparatus according to claim 10, wherein said reference pressing force determining means comprises means for determining, as said reference pressing force of said pressing device, a pressing force of said pressing device at a time when a greatest one of said respective amplitudes of said successive pulses of said pressure signal is obtained while said pressing force of said pressing device is changed.

13. An apparatus according to claim 9, wherein said second straight line determining means comprises:
second pressure range determining means for determining a second pressure range based on said successive pulses of said pressure signal obtained by said control device while said pressing force of said pressing device is changed; and
increasing portion determining means for determining, as said increasing portion of said at least one of (a) said upper-peak curve and (b) said lower-peak curve, a portion of said at least one of (a) said upper-peak curve and (b) said lower-peak curve which portion corresponds to said second pressure range.

14. An apparatus according to claim 13, wherein said second pressure range determining means comprises means for determining said second pressure range which has a lower limit greater by a predetermined amount than an upper limit of said first pressure range, and an upper limit represented by a magnitude of said increasing portion corresponding to an upper limit of said pressing force of said pressing device.

15. An apparatus according to claim 1, wherein said first straight line determining means comprises means for determining, as said first straight line, a regression line of said level portion of said at least one of (a) said upper-peak curve and (b) said lower-peak curve.

16. An apparatus according to claim 1, wherein said second straight line determining means comprises means for determining, as said second straight line, a correlation line of said increasing portion of said at least one of (a) said upper-peak curve and (b) said lower-peak curve.

17. An apparatus according to claim 1, further comprising an output device which outputs said at least one of said systolic and said diastolic blood pressure of the subject determined by said blood pressure determining means.

18. An apparatus according to claim 17, wherein said output device comprises at least one of (a) an image display which displays said at least one of said systolic and said diastolic blood pressure of the subject and (b) a recorder which records, on a recording medium, said at least one of said systolic and said diastolic blood pressure of the subject.

19. An apparatus according to claim 1, wherein said control device comprises timer means for operating, at regular intervals of time, said pressing device to press said surface-pressure sensor against the artery via the body surface.

20. An apparatus according to claim 1, wherein said pressing device comprises:

a housing;

an elastic diaphragm through which said surface-pressure sensor is secured to an inner surface of said housing which cooperates with said diaphragm and said sensor to define a pressure chamber;

a fluid supply which supplies a pressurized fluid to said pressure chamber to press said sensor against the artery via the body surface; and a pressure regulator which regulates a fluid pressure in said pressure chamber, said fluid pressure of said pressure chamber corresponding to said pressing force of said pressing device.

* * * * *